(12) United States Patent
Hochman et al.

(10) Patent No.: US 11,510,593 B2
(45) Date of Patent: Nov. 29, 2022

(54) SYSTEMS, METHODS AND COMPUTER READABLE MEDIA FOR NON-CONTACT PHYSIO-BEHAVIORIAL MONITORING OF A SUBJECT

(71) Applicant: Emory University, Atlanta, GA (US)

(72) Inventors: Shawn Hochman, Decatur, GA (US); William Goolsby, Atlanta, GA (US); Michael McKinnon, Atlanta, GA (US); Camden MacDowell, Atlanta, GA (US); Heidi Kloefkorn-Adams, Atlanta, GA (US)

(73) Assignee: Emory University, Atlanta, GA (US)

( * ) Notice: Subject to any disclaimer, the term of this patent is extended or adjusted under 35 U.S.C. 154(b) by 285 days.

(21) Appl. No.: 16/095,906

(22) PCT Filed: Apr. 25, 2017

(86) PCT No.: PCT/US2017/029462
§ 371 (c)(1),
(2) Date: Oct. 23, 2018

(87) PCT Pub. No.: WO2017/189608
PCT Pub. Date: Nov. 2, 2017

(65) Prior Publication Data
US 2021/0219871 A1    Jul. 22, 2021

Related U.S. Application Data

(60) Provisional application No. 62/327,269, filed on Apr. 25, 2016.

(51) Int. Cl.
*A61B 5/11* (2006.01)
*A61B 5/0205* (2006.01)
(Continued)

(52) U.S. Cl.
CPC .......... *A61B 5/1113* (2013.01); *A61B 5/0205* (2013.01); *A61B 5/05* (2013.01);
(Continued)

(58) Field of Classification Search
CPC ....... A61B 5/1113; A61B 5/742; A61B 5/746; A61B 5/05; A61B 5/0205; A61B 5/7264;
(Continued)

(56) References Cited

U.S. PATENT DOCUMENTS

| | | | |
|---|---|---|---|
| 2012/0215092 A1* | 8/2012 | Harris, III | H04B 7/12 600/410 |
| 2013/0030257 A1* | 1/2013 | Nakata | G01S 7/003 600/301 |
| 2014/0055269 A1* | 2/2014 | Howie | A61B 5/24 702/65 |

* cited by examiner

*Primary Examiner* — Rex R Holmes
(74) *Attorney, Agent, or Firm* — Emory Patent Group

(57) ABSTRACT

The systems and methods can provide continuous, efficient, accurate, non-contact, monitoring of one or more cardio-respiratory and/or behavior parameters associated with a subject in a defined environment using at least non-contact sensor data and provide feedback based on the determined parameters. The system can include one or more sensor modules disposed within defined environment(s). The system may further include one or more sensors disposed at a specific spatial location in the defined environment. The sensor(s) may include non-contact electric field sensor(s) configured to record non-contact sensor data related to one or more periods of stillness and/or movement of the subject. The system may further include one or more processors configured to determine cardiorespiratory respiratory parameters and/or behavior parameters using the non-contact sensor data. Because the systems and methods also allow for continuous collection of measurable variables,
(Continued)

they can provide a high-throughput quantifiable record of the subject's physio-behavioral self.

18 Claims, 5 Drawing Sheets

(51) Int. Cl.
  *A61B 5/05* (2021.01)
  *A61B 5/00* (2006.01)
(52) U.S. Cl.
  CPC ............ *A61B 5/7264* (2013.01); *A61B 5/742* (2013.01); *A61B 5/746* (2013.01); *A61B 2503/40* (2013.01); *A61B 2503/42* (2013.01); *A61B 2560/0242* (2013.01)
(58) Field of Classification Search
  CPC ............ A61B 2503/42; A61B 2503/40; A61B 2560/0242
  See application file for complete search history.

SYSTEMS, METHODS AND COMPUTER READABLE MEDIA FOR NON-CONTACT PHYSIO-BEHAVIORIAL MONITORING OF A SUBJECT

CROSS-REFERENCE TO RELATED APPLICATIONS

This application is the National Stage of International Application No. PCT/US2017/029462 filed Apr. 25, 2017, which claims the benefit of U.S. Provisional Application No. 62/327,269 filed Apr. 25, 2016. The entirety of each of these applications is hereby incorporated by reference for all purposes.

BACKGROUND

Tracking cardiorespiratory parameters and behaviors of animals can provide predictive and diagnostic information, for example, of adverse clinical events, such as cardiovascular disease. However, most monitoring approaches can be expensive and impractical for large-scale studies, for example, that require monitoring rodent physiology. For example, current technologies for monitoring rodent physiology can require contacting sensors, separate airtight chamber environments that are separate from home cages, separate cages, and/or surgically invasive approaches. These approaches can therefore result in restraint of experimental design, increase in cost, and decrease of throughput.

SUMMARY

Thus, there is need for systems, methods, and computer readable media that can accurately and economically determine cardiorespiratory parameters and/or behaviors of subjects.

The disclosure relates to systems and methods that can continuously monitor physio-behavioral variables using non-contact, non-invasive sensors.

In some embodiments, the system may relate to a system configured to monitoring one or more cardiorespiratory parameters, behavior parameters, and health events based on the cardiorespiratory and/or behavior parameters, associated with at least one subject in at least one defined environment. In some embodiments, the system may include one or more sensor modules disposed within and/or on one or more defined environments. Each sensor module may include one or more sensors disposed at a specific spatial location in the defined environment and configured to record sensor data of the subject. The one or more sensors may include one or more non-contact electric field sensors. The one or more non-contact electric field sensors may be configured to record non-contact sensor data related to one or more periods of stillness and/or movement. The system and/or each sensor module may include one or more processors configured to determine at least cardiorespiratory parameters and/or behavior parameters using the non-contact sensor data. The one or more processors may be configured to determine one or more cardiorespiratory parameters when the non-contact sensor data relates to one or more periods of stillness. The one or more cardiorespiratory parameters may include respiratory rate and heart rate.

In some embodiments, the one or more processors may be configured to determine one or more behavior parameters when the non-contact sensor data relates to one or more periods of movement. In some embodiments, the one or more processors may be configured to determine whether the non-contact sensor data relates to one or more periods of stillness and/or movement based one or more thresholds and/or a location of the one or more non-contact sensors within the defined environment.

In some embodiments, the system may include one or more environmental actuators configured to cause a change in one or more environmental conditions within the defined environment and/or deliver an alert according to operation instructions based on (i) stored triggering conditions and (ii) the non-contact sensor data, the one or more cardiorespiratory parameters, and/or the one or more behavior parameters. In some embodiments, the one or more processors may be configured to determine the operation instructions by comparing at least the non-contact sensor data to the stored triggering conditions.

In some embodiments, the system may include a metal shielding material and/or an electrical shielding material. The metal shielding material and/or electrical shielding material may be disposed to at least partially surround the defined environment. In some embodiments, the metal shielding material and the electrical shielding material may be integrated into a single piece.

In some embodiments, the one or more defined environments may include a first defined environment and a second defined environment separated by the first environment by the electrical shielding material. Each of the first environment and the second environment may include the one or more sensors. The one or more processors may be configured to communicate with the one or more sensors disposed in the first environment and the second environment.

In some embodiments, the system may include a display. The display may be configured to display the non-contact sensor data and/or the one or more cardiorespiratory parameters for the first environment and the second environment.

In some embodiments, the one or more sensor modules may include a communication interface and one or more environmental actuators configured to cause a change in one or more environmental conditions within the defined environment based on one or more operating instructions.

In some embodiments, the system may include an analysis module that includes a processor that is configured to receive the sensor data from the one or more sensor modules using the communication interface. The analysis module may be configured to compare (i) at least the non-contact sensor data, the one or more cardiorespiratory parameters, and/or the one or more behavior parameters to (ii) one or more stored triggering conditions to determine the one or more operating conditions.

In some embodiments, the one or more sensors may include tracking sensors configured to detect a subject with respect to the defined environment, a location of the subject within the defined environment, among others, or a combination thereof.

In some embodiments, the system may relate to a system configured to monitoring one or more cardiorespiratory parameters, behavior parameters, and health events based on the cardiorespiratory and/or behavior parameters, associated with at least two subjects that are each disposed in a defined environment. In some embodiments, the system may include a processing module including a one or more processors, memory, and one or more environmental actuators. The processing module may be configured to monitor two or more different defined environments. The system may further include one or more sensors disposed at a specific spatial location in the each of the first defined environment and the second defined environment. The one or more sensor s may be configured to record sensor data of the subject disposed in each environment. The one or more sensors may include one or more non-contact electric field sensors. The one or more non-contact electric field sensors may be configured to record non-contact sensor data related to one or more periods of stillness and/or movement. The one or more processors may be configured to determine at least cardiorespiratory parameters and/or behavior parameters for each subject using the non-contact sensor data. The one or more processors may be configured to determine one or more cardiorespiratory parameters for each subject when the non-contact sensor data for the each subject relates to one or more periods of stillness. The one or more cardiorespiratory parameters may include respiratory rate and heart rate.

In some embodiments, the one or more processors may be configured to determine one or more behavior parameters for each subject when the non-contact sensor data for the each subject relates to one or more periods of movement. In some embodiments, the one or more processors may be configured to determine whether the non-contact sensor data relates to one or more periods of stillness and/or movement based one or more thresholds and/or a location of the one or more non-contact sensors within the defined environment.

In some embodiments, the system may include one or more environmental actuators configured to cause a change in one or more environmental conditions within the first and/or second defined environment and/or deliver an alert according to operation instructions based on (i) stored triggering conditions and (ii) the non-contact sensor data, the one or more cardiorespiratory parameters, and/or the one or more behavior parameters associated with each subject. In some embodiments, the one or more processors may be configured to determine the operation instructions by comparing at least the non-contact sensor data associated with each subject to the stored triggering conditions associated with the each subject and/or defined environment.

In some embodiments, the system may include a metal shielding material and/or an electrical shielding material. The metal shielding material and/or electrical shielding material may be disposed to at least partially surround the first and/or second defined environments. In some embodiments, the metal shielding material and the electrical shielding material may be integrated into a single piece.

In some embodiments, the first defined environment and the second defined environment may be separated by at least the electrical shielding material.

In some embodiments, the system may include an analysis module that includes a processor that is configured to receive the sensor data from the one or more sensor modules using a communication interface. The analysis module may be configured to compare (i) at least the non-contact sensor data, the one or more cardiorespiratory parameters, and/or the one or more behavior parameters to (ii) one or more stored triggering conditions to determine the one or more operating conditions.

In some embodiments, the one or more sensors may include tracking sensors configured to detect a subject with respect to each defined environment, a location of the subject within each defined environment, among others, or a combination thereof.

In some embodiments, the method may relate to a method for monitoring one or more cardiorespiratory parameters, behavior parameters, and health events based on the cardiorespiratory and/or behavior parameters, associated with a subject. In some embodiments, the method may include acquiring sensor data from one or more sensor modules disposed within and/or on one or more defined environments. Each sensor module may include one or more sensors disposed at a specific spatial location in the defined environment and configured to record sensor data of the subject. The one or more sensors may include one or more non-contact electric field sensors. The one or more non-contact electric field sensors may be configured to record non-contact sensor data related to one or more periods of stillness and/or movement. The method may include determining, using a processor, at least cardiorespiratory parameters and/or behavior parameters using the non-contact sensor data. The one or more cardiorespiratory parameters may be determined when the non-contact sensor data relates to one or more periods of stillness. The one or more cardiorespiratory parameters may include respiratory rate and heart rate.

In some embodiments, the one or more behavior parameters may be determined when the non-contact sensor data relates to one or more periods of movement. In some embodiments, the non-contact sensor data may be determined to relate one or more periods of stillness and/or movement based one or more thresholds and/or a location of the one or more non-contact sensors within the defined environment.

In some embodiments, the method may include instructing one or more environmental actuators to cause a change in one or more environmental conditions within the defined environment and/or deliver an alert according to operation instructions based on (i) stored triggering conditions and (ii) the non-contact sensor data, the one or more cardiorespiratory parameters, and/or the one or more behavior parameters. In some embodiments, the method may include determining the operation instructions by comparing at least the non-contact sensor data to the stored triggering conditions.

In some embodiments, wherein one or more sensor modules may include a metal shielding material and/or an electrical shielding material. The metal shielding material and/or electrical shielding material may at least partially surround the defined environment. In some embodiments, the metal shielding material and the electrical shielding material may be integrated into a single piece.

In some embodiments, the one or more defined environments may include a first defined environment and a second defined environment separated by the first environment by the electrical shielding material. Each of the first environment and the second environment may include the one or more sensors. In some embodiments, the receiving sensor data may include receiving the sensor data from each of the one or more sensors disposed in the first environment and the second environment.

In some embodiments, the method may include displaying the non-contact sensor data and/or the one or more cardiorespiratory parameters for the first environment and the second environment.

In some embodiments, the method may include comparing the (i) at least the non-contact sensor data, the one or more cardiorespiratory parameters, and/or the one or more behavior parameters to (ii) one or more stored triggering conditions to determine one or more operating conditions. The method may include causing a change in one or more environmental conditions within the defined environment based on the one or more operating instructions:

In some embodiments, the one or more sensors may include tracking sensors configured to detect the subject using identification information, with respect to the defined environment, a location of the subject within the defined environment, among others, or a combination thereof. The method may further include associating the identification information to the sensor data for the subject.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
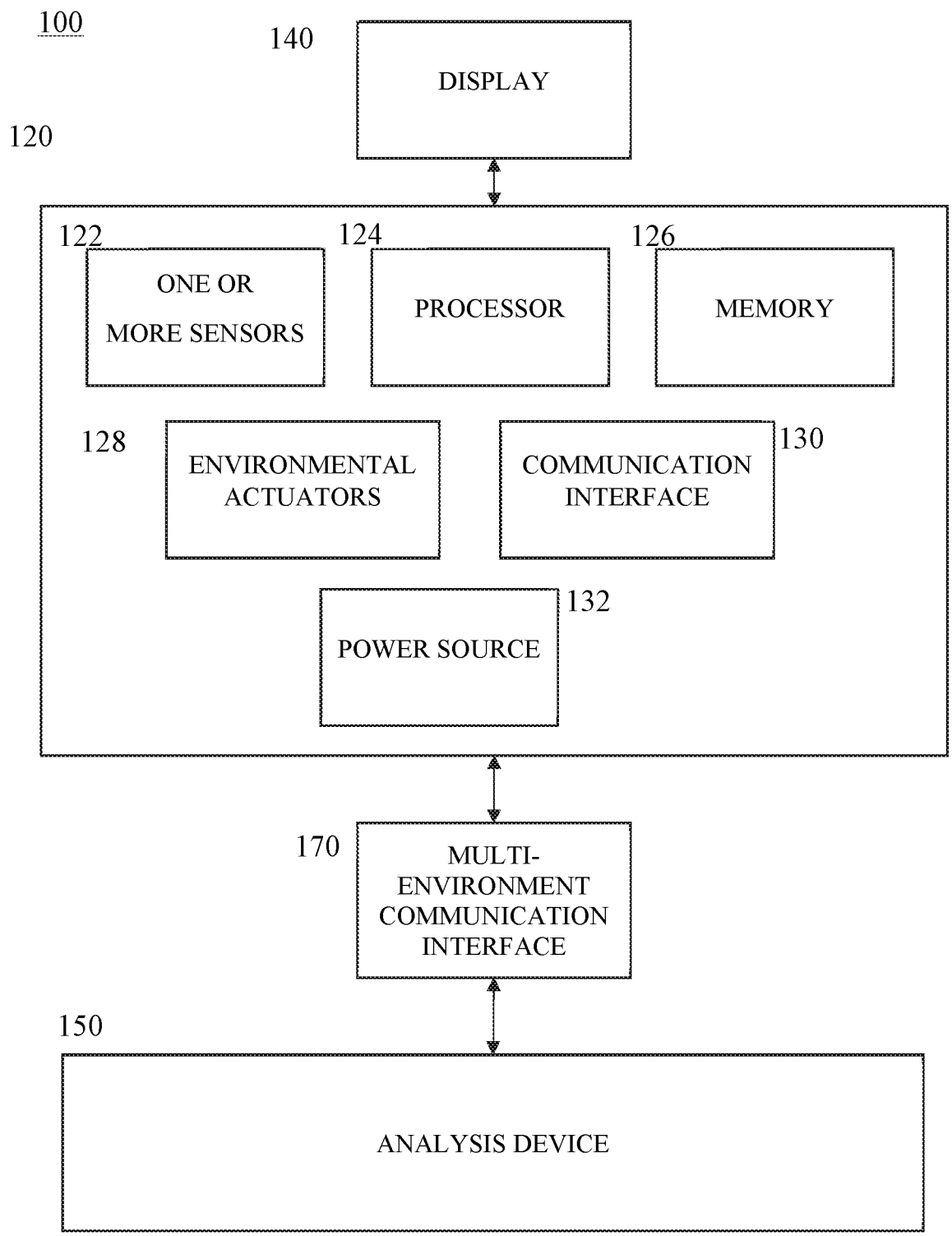
FIG. 1 shows an example of a system for determining parameters using one or more sensors including non-contact electric field sensor to some embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The systems and methods of the disclosure can allow for continuous, combined non-contact, non-invasive monitoring, quantification, and/or categorization of cardiorespiratory and/or behavioral parameters in a defined environment and providing feedback based on those parameters, for example, by altering or tuning one or more environmental conditions within that defined environment based on triggering conditions. The term "non-contact" is used to indicate activities outside of, and not requiring direct physical contact with, the subject body. By altering or tuning the environmental conditions, the physio-behaviors of the animals may be tuned.

The systems and methods also allow for monitoring to be performed in an animal's home-cage environment. Additionally, the systems and methods also allow for monitoring dual housing, which permit continued affirmative and prosocial interactions.

The systems and methods also allow for continuous collection of measurable variables and can therefore provide a high-throughput quantifiable record of the animal's physio-behavioral self. The systems and methods can therefore shed insight in its role in experimental variability.

The record can also provide predictive power on disease emergence This datalogging of the animal's physio-behavioral self can be collected for extended periods to further profile temporal dynamics in emerging dysfunction. Data can then be used to identify changes that precede and therefore predict dysfunction. This can be used to shift health management towards individualized physiological monitoring by predicting, preventing, and better managing disease using this record.

The non-invasive and affordable near-continuous home-cage recordings of an animal's physio-behavioral self as part can also revolutionize our understanding of the origins of inter-animal variability including in our understanding of vulnerability and resistance to disease. For example, this can result in a transfer of experimental studies to the vivarium home cage thereby achieving a more individualized understanding of behavior and phenotyping inter-individual and inter-lab differences.

As used herein, a "subject" refers to a human or animal. The animal may include but is not limited to: primate (e.g., such as chimpanzees, cynomologous monkeys, spider monkeys, macaques, etc.), rodent (e.g., such as mice, rats, woodchucks, ferrets, rabbits and hamsters), domestic animal or game animal (e.g., such cows, horses, pigs, deer, bison, buffalo, feline species, (e.g., domestic cat), canine species, (e.g., dog), fox, wolf, avian species (e.g., such as, chicken, emu, ostrich, etc.), fish (e.g., such as trout, catfish, salmon, etc.), among others, or any combination thereof. Although some portions of the present disclosure refer to animals, such as rodents, the disclosure can be applied to any mammal, including humans and non-human primates, as well as other animals. As an example, mammals other than humans may be used as subjects that represent animal models of disorders or diseases.

FIG. 1 shows a system 100 configured to monitor one or more cardiorespiratory, behavioral parameters related to a subject disposed in at least one defined environment or space by continuously analyzing sensor data from one or more sensors provided within the defined environment. One or more cardiorespiratory parameters may include but is not limited to heart rate, respiratory rate, blood pressure, among others, or a combination thereof.

The behavioral parameters may relate to behaviors associated with motor or physical activity. Motor or physical activity refers to any physical activity, such as a physical change or any movement by the subject. The behaviors may include but is not limited to: approach, circling, chewing, digging/burying, drinking, eating, freezing, gait (normal, abnormal), grooming (face, anogenital, abnormal), huddling, intake, jump (horizontal, vertical, stereotyped), lever-pressing, locomotion (walk, run), nose-poking, rearing (normal, stereotyped), seizures (tonic, clonic), self-biting, scratching (normal, stereotyped), stretch-attend, sleeping, sniffing, startle, stereotypic behavior, tail position, temperature, twitching, yawning, barking, among others, or any combination thereof.

The defined space or environment refers to any space or environment in which sensing of a subject is to be performed. In some embodiments, the defined environment may be defined by one or more walls, barriers, panels, etc. (such as a cage, a kennel, a crate, a vehicle, a stall, a room, among others, or a combination thereof); one or more areas within a space or environment defined by one or more objects (such as a nest, mattress, wheel chair, seat, or floor covering, eating area, drinking area, exercise area, excretory area, among others, or a combination thereof); among others; or a combination thereof.

The system 100 may further determine one or more health events based on one or more of cardiorespiratory parameters, behavior parameters, and/or any combination of cardiorespiratory and/or behavior parameters. The one or more health events may include but is not limited to presence and/or state of a disease, presence and/or state of a disorder, a state of a physiological parameter, response to a therapeutic (e.g., drug), among others, or a combination thereof. For example, the one or more health events include but is not limited to cardiorespiratory disorders (e.g., hypertension), neurological disorders, chronic pain, stress, sleep state, other motor and autonomic disease states, sleep state, sleep architecture, among others, or any combination thereof. In some embodiments, the system may determine the one or more health events based on an incidence or a frequency of an incidence of behavior parameters and/or cardiorespiratory parameters.

Based on the sensor data and/or the one or more cardiorespiratory and/or behavioral parameters, and/or the health events determined from the sensor data, the system 100 may be configured to change one or more environmental conditions within the defined environment. For example, when the defined environment is a cage, crate or kennel, or a room, the system 100 may be configured to cause one changes in the temperature, humidity, visual, olfactory, auditory, or tactile environmental conditions within the defined environment. For example, the system 100 may be configured to cause or more of the following: change the light (e.g., different colors and/or intensities), change the heat, change the humidity, deliver an odorant, trigger a nebulizer, provide tactile stimuli (e.g., mechanical stimulation, air puffs of various wind and velocity, vibration, temperature, and duration), provide auditory sounds (e.g., an alarm), and change in delivery of food and/or water, among others, or a combination thereof. This way, the system 100 can provide feedback control in response to the sensor data. In some embodiments, for example, systems that are for rodent cages, the cage may include light, such as an LED array capable of spanning the rodent visual range from near UV to green as well as other colors, that can be controlled by the system 100.

In some embodiments, the system 100 for monitoring the cardiorespiratory and/or behavior parameters for one or more defined environment may include one or more sensor modules 120 and one or more analysis modules 150. In some embodiments, the analysis module 150 may have connectivity to the one or more sensor modules 120 via a communication network. By way of example, the communication network of system 100 can include one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, NFC/RFID, RF memory tags, touch-distance radios, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Although the systems/devices of the system 100 are shown as being directly connected, the systems/devices may be indirectly connected to one or more of the other systems/devices of the system 100. In some embodiments, a system/device may be only directly connected to one or more of the other systems/devices of the system 100.

It is also to be understood that the system 100 may omit any of the systems and/or devices illustrated and/or may include additional systems and/or devices not shown. It is also to be understood that more than one device and/or system may be part of the system 100 although one of each device and/or system is illustrated in the system 100. It is further to be understood that each of the plurality of devices and/or systems may be different or may be the same. A general framework of the systems and methods described herein is illustrated in FIG. 1.

In some embodiments, the sensor module(s) 120 may include one or more sensors 122. The one or more sensors 122 may be configured to detect sensor data related to one or more cardiorespiratory and/or behavior parameters for one or more subjects and/or in relation to distinct spatial locations within the defined environment. The one or more sensors 122 may include one or more non-contact electric field sensors (such as electric potential integrated circuit sensors (e.g., PLESSY EPIC™)), accelerometers, sound sensors, temperature sensors, force sensors, humidity sensors, feeding sensors (e.g., sensors configured to detect food dispensing), tagging or tracking sensors (e.g. RFID), and other physiological sensors, among others, or a combination thereof.

The one or more sensors 122 may include one or more electric field sensors (also referred to as "one or more non-contact electric field sensors") that are disposed within the defined environment so as to not contact the subject. For example, in some embodiments, the one or more non-contact electric field sensors may be configured to generate sensor data related to the subject that can be used by the system 100 to determine cardiorespiratory and/or behavior parameters. By way of example, the one or more non-contact electric field sensors may generate sensor data during periods of movement and stillness of the subject (referred to as movement data and stillness data).

In some embodiments, the system 100 using the sensor module(s) 120 and/or the analysis module 150 may process the non-contact electric field sensor data to determine whether the subject is in a period of movement or motor activity (e.g., movement or physical activity) and/or a period of stillness based one or more thresholds and/or a (spatial) location of the one or more non-contact electric field sensors that records the sensor data (also referred to as non-contact sensor data) within the environment. Each threshold may relate to a voltage signal and/or frequency, and/or a defined range of voltage signals and/or frequencies. For example, the system 100 may determine that the sensor data relates to a subject in a period of stillness (e.g., corresponds to stillness data), when the sensor data: (i) is recorded at one or more specific location(s); and/or (ii) is below a specific voltage signal and/or frequency, and/or within specific range(s) of voltage signals and/or frequencies. The system 100 may determine that the sensor data relates to a subject in a period of motor activity (e.g., corresponds to movement data) when the sensor data: (i) is recorded at one or more specific location(s); and/or (ii) is above a specific voltage signal and/or frequency, and/or within specific range(s) of voltage signals and/or frequencies. For example, the specific location(s) may correspond to the location of the subject, the location of the sensor(s) that recorded the data, among others, or a combination thereof.

Using at least the stillness data, the system 100 may determine cardiorespiratory parameters. Using at least the movement data, the system 100 may determine behavior parameters. For example, the one or more non-contact electric field sensors may be configured to collect sensor data related to a subject to determine one or more of the following: heart rate, respiration rate, blood pressure (e.g., using also pulse wave velocity); overall motor activity; specific motor patterns that reflect various behaviors including grooming, rearing, feeding, and shivering; stress monitoring; and sleep state and sleep architecture; among others; or any combination thereof.

In one example, the sensor module(s) 120 may include one or more non-contact electric field sensors that is disposed at a specific location within the defined environment and configured to detect both cardiorespiratory parameters and behavior parameters. For example, each non-contact electric field sensor may use one or more channels for detecting respiratory rate and/or heart rate, and one or more channels for detecting motor activity. In a further example, the system 100 may segment the data received from that sensor into movement data and stillness data. This way, a single circuit can be used to detect sensor data to both parameters.

In another example, the sensor module(s) 120 may include two or more non-contact electric field sensors that are disposed at a specific location within the defined environment so that each circuit is dedicated to a specific sensor data collection (e.g., motor or stillness data) and/or parameter determination (e.g., cardiorespiratory and/or behavior parameter). At least a first electric field sensor may be configured to detect respiratory rate and/or heart rate using one or more channels, and at least a second electric field sensor may be configured to detect motor activity using one or more channels. This way, each sensor may be dedicated to detecting sensor data specific to one type of parameter (e.g., cardiorespiratory or behavior parameter).

By way of example of a location-based processing, the system 100 may process data received from one or more sensors disposed at a nest (e.g., in a cage) and/or a bed (e.g., in a bedroom) in the defined environment as stillness data. In this example, the system 100 may process the received sensor data for at least one or more cardiorespiratory parameters. By way of another example, the system 100 may process the data received from one or more sensors disposed at a running wheel (e.g., in a cage) and/or a treadmill in the defined environment as movement data. In this example, the system 100 may process the received sensor data for at least one or more behavior parameters.

In some embodiments, the one or more sensors 122 may include one or more tagging/tracking sensors configured to detect a subject, for example, with respect to the defined environment, a location of the subject within the defined environment, among others, or a combination thereof. The one or more tracking sensors may include but is not limited to a radio frequency identification (RFID) reader. For example, the RFID reader may be configured to communicate directly with RFID tags disposed on the subject to identify that subject. In this example, the subject may be identified relative to a sensor and/or defined environment, and the sensor data can be associated with that subject. This way, for example, the system 100 can monitor more than one subject in a defined environment and/or monitor an individual subject in a defined environment having a plurality of different subjects without interference.

In some embodiments, the one or more sensors 122 may be configured to monitor one or more environmental conditions and/or events (also referred to as "environmental sensors") provided in the defined area. For example, the one or more environmental sensors may include but is not limited to: a temperature sensor, humidity sensor, light sensor, chemical sensor (e.g. release of volatile molecules in sweat, fur, and from excretory systems), sound-wave sensor (e.g., to detect environmental events that include vocalizations including ultrasonic vocalizations and barking), among others, or a combination thereof.

In some embodiments, the sensor module(s) 120 may include one or more processors 124 configured to process the sensor data received from the one or more sensors 122 in a plurality of channels. The one or more processors 124 may be any known central processing unit, a processor, or a microprocessor. For example, at least one of the processors 124 may be configured for signal processing. The processor(s) 124 may be configured to digitize the sensor data received from the one or more sensors 122 in one or more channels. For example, the processor(s) 124 may be configured to convert the analog sensor data related to the cardiorespiratory and/or behavior parameters, received from the one or more electric field sensors to digital sensor data. As an example, the processor 124 may be a 32-bit ARM processor running at 84 MHz and have onboard 12-bit analog-to-digital converter (ADC) that can provide up to 20 input channels. In such a scenario, the ADC may process the signals from the one or more sensors 122 via the one or more data channels so as to generate digitized sensor data from which the one or more cardiorespiratory and/or behavioral parameters may be determined by the analysis module 150. In another example, one or more of the processor(s) 124 may be external to the sensor module 120.

In some embodiments, the sensor module(s) 120 may include a memory 126 for storing the raw and processed sensor data. For example, the memory 126 may include a random access memory (RAM) on which the sensor data received from the one or more sensors 122 may be buffered. In another example, the memory 126 may include a removable memory drive (e.g., USB memory drive), among others, or any combinations thereof. For example, the memory 126 may include a removable memory drive on which the buffered, raw, and/or processed data may be stored.

In some embodiments, the processor(s) 124 may be configured to use direct memory access (DMA) and interrupt to sample sensor signals and store the data into double buffers (e.g., a first buffer and a second buffer) in the memory 126. For example, the sensor module 120 may perform the processing without processor registers, so the collection of the sensor data can take very little processor time, less than 1%.

The processor(s) 124 may double buffer the sensor data received from the one or more sensors 124. For example, when one of the buffer is full, the processor(s) 124 may cause that set or packet of raw sensor data to be transmitted to the analysis module 150 via a communication interface 130, for example, over a radio link. The processor(s) 124 may also transmit additional data, such as environmental conditions and/or physiological condition data (e.g., temperature, humidity, food pellets eaten, movement, etc.), to the analysis module 150 to determine additional cardiorespiratory and/or behavior parameters and/or one or more health events.

In some embodiments, the processor(s) 124 may also use a copy of the set of data to determine at least cardiorespiratory and/or behavior parameters. For example, the processor(s) 124 may use time and frequency processing to determine the cardiorespiratory parameter(s), such as respiratory rate (RR) and/or heart rate (HR), and/or behavior data. In some embodiments, the processor(s) 124 may use Fast Fourier Transform (FFT), Buneman Frequency Estimation and amplitude analysis of total energy in the signal to determine the one or more respiratory and/or behavior parameters.

In some embodiments, the processor(s) 124 and/or the analysis module 150 may be configured to filter the processed sensor data from the one or more non-contact electric field sensors to determine whether the sensor data relates to different behaviors and/or cardiorespiratory parameters. In some embodiments, after the data is transformed into frequencies, the processor 124 and/or the analysis module 150 may compare the data to specific threshold ranges corresponding to specific respiratory and/or behavior parameters to determine one or more respiratory and/or behavior parameters. For example, for rodents, the processor 124 and/or the analysis module 150 may process the frequency associated with the received sensor data using the following thresholds: about 0.1 to 1 Hz to correspond to respiratory depression, about 1 to about 7 (e.g., 6.4) Hz to correspond to respiratory rate, about 4 (e.g., 4.3) to 15 (e.g., 12) Hz corresponds to heart rate and various motor rhythms, and about 10 to 25 Hz corresponds to chewing.

The sensor module(s) 120 may include one or more environmental actuators 128 configured to cause one or more changes to one or more environmental conditions within the defined area and/or room in which the defined area is disposed based on the parameters and/or health events determined by the processor(s) 124 and/or the analysis module 150 using stored triggering conditions that are default and/or set by a user (which can be the subject and/or related to the subject (e.g., researcher, parent, health care provider, etc.)). For example, the stored triggering conditions may be specific to the subject and/or defined environment. By way of example, the stored triggering conditions may be stored in the memory 126 of the processor and/or memory of the analysis module 150. Each triggering condition may include criteria (e.g., threshold value and/or range for cardiorespiratory and/or behavior parameter; and/or presence a health event) and may be associated with one or more operation instructions for the one or one more environmental actuators 128. For example, the operation instructions can include but are not limited to providing an alert, changing the lighting (e.g., by turning on and/or off one or more lights, and/or changing light properties (e.g., color, intensity, etc.), changing the temperature (e.g., increasing and/or decreasing the detected temperature), changing the humidity (e.g., by increasing and/or decreasing the detected level), changing the smell (e.g., the delivering an odorant), the availability of resources (e.g., feeding and/or water), providing a sound, among others, or a combination thereof. For example, in operation, the processor(s) 124 and/or the analysis module 150 may determine that the one or more cardiorespiratory and/or behavior parameters and/or one or more health events meet one or more triggering conditions and may cause operation instructions to be sent to the one or more environmental actuators 128 to cause one or more environmental conditions to change in the defined environment according to the operation instructions associated with the one or more trigger conditions.

In some embodiments, the sensor module(s) 120 may communicate with and/or include a display 140. For example, the sensor module(s) 120 may transmit the determined cardiorespiratory parameters and/or behavior parameters for each set or packet of data (e.g., the heart rate and/or respiratory rate) to be displayed on the display 140. In this way, the parameters and/or sensor data may be displayed in real-time.

The display 140 may be a liquid crystal display (LCD) screen disposed on the sensor module 120, external to the defined environment (e.g., cage or crate), within the defined environment (e.g., room), among others, or a combination thereof. By way of example, if the display is external, the display 140 may be part of a user device (e.g., a mobile handset, tablet, and/or tablet computer). In some embodiments, a plurality of the sensor modules 120 may communicate with the display 140 so that the display 140 displays the sensor data and/or parameters for the plurality of sensor modules 120.

By way of example, a plurality of cages for rodents may be disposed in one or more rooms and each of which may include a sensor module 120. Rather than having a display 140 for each sensor module 120, at least a subset of the sensor modules 120 may communicate to the display 140 so that the data for that subset of the cages may be displayed on a single display 140 for ease of monitoring.

In some embodiments, the sensor module 120 may include a communication interface 130 for communicating with the analysis module 150, communication interface 170 and/or the display 140. For example, the communication interface 130 may be a wired and/or wireless interface, a switched circuit wireless interface, a network of data processing devices, such as LAN, WAN, the internet, or combination thereof. The communication interface 130 may be configured to execute various communication protocols, such as Bluetooth, wireless, and Ethernet, in order to establish and maintain communication with at least another module on the network.

In some embodiments, the sensor module 120 may include a power source 132. The power source 132 include one or more batteries, such as a rechargeable lithium-ion type, electrical power source, among others, or a combination thereof. For example, if the battery is rechargeable, the battery may have a capacity to run the sensor module for about a week.

In some embodiments, the analysis module 150 may be configured to process the digitized sensor data and/or the frequencies associated with the received sensor data to determine the cardiorespiratory parameter(s) and/or behavior parameter(s) and/or the health event(s). In some embodiments, the analysis module 150 may be a part of the sensor module(s) 120. For example, the one or more processors 124 may be configured to be perform the processing discussed herein with respect to the analysis module 150. In some embodiments, the analysis module 150 may be an external device configured to communicate with one or more sensor modules 120. For example, the analysis module 150 may communicate with and process sensor data received from a plurality of sensor modules 120 disposed on a plurality of cages disposed in a room (see FIG. 2).

In some embodiments, the analysis module 150 may be any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, or any combination thereof, including the accessories and peripherals of these devices, or any combination thereof. The analysis module 150 can also support any type of interface to the user (such as "wearable" circuitry, etc.). By way of example, the analysis module 150 and one or more sensing modules 120 can communicate with each other and other components of the communication network using well known, new or still developing protocols.

In some embodiments, the analysis module 150 and/or the one or more processors 124 may be configured to determine feedback based on the one or more determined cardiorespiratory and/or behavior parameters and/or health events using the one or more triggering conditions. For example, the analysis module 150 and/or the processor(s) 124 may transmit operation instructions to the environmental actuator(s) 128 to cause change in one or more environmental conditions provided in the defined environment and/or room, cause an alert to be transmitted to a user (e.g., researcher, subject, health provider, etc.) regarding a determined parameter and/or health event, among others, or a combination thereof. For example, the alert may include but is not limited to a visual alert, a sound alert, among others, or any combination thereof. By way of example, the analysis module 150 may be configured to cause an alert to be transmitted to the display 140 and/or sensor module(s) 120 to alert the user.

In some embodiments, the system 100 may optionally include a multi-environment communication interface 170 that can receive the data from a plurality of sensor modules 120 for more than one defined environment. The communication interface 170 may be configured to communicate with a plurality of sensor modules 120 so as to efficiently transmit the raw and/or processed data between the sensor modules 120 (e.g., the display 140 and/or environmental actuator(s) 128) and/or the analysis module 150. For example, the communication interface 170 may be a transceiver.

Figure 2:
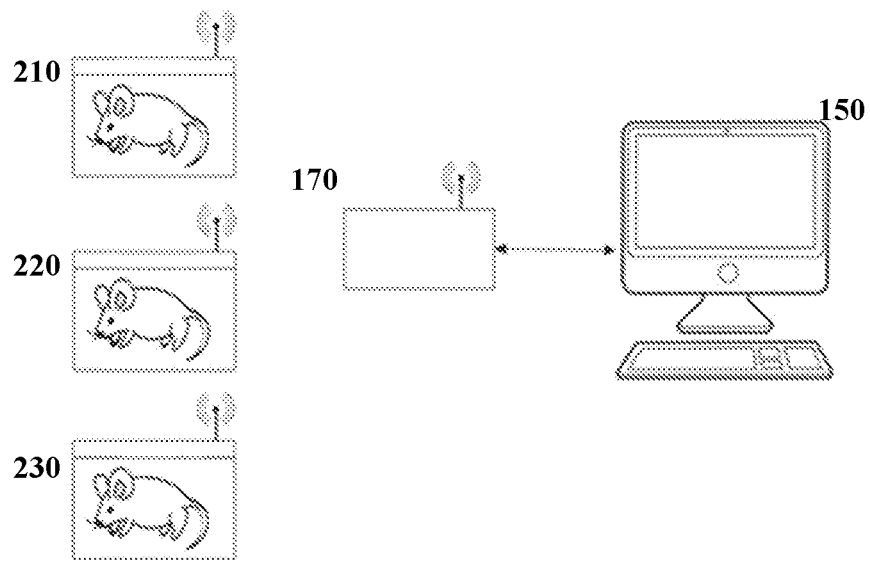
FIG. 2 shows an example of a system configuration according to some embodiments.

FIG. 2 shows an example 200 of a multi-environment arrangement. As shown in FIG. 2, the communication interface 170 may wirelessly receive sensor data from sensor modules 120 disposed within and/or on each of environments 210, 220, and 230. In this example, the environments 210, 220 and 230 are cages for rodents. It will be understood that the environments may be different and may include more or less cages and sensor modules.

The sensor module 120 for each environment 210, 220 and 230 can wirelessly transmit a packet or set of sensor data to the communication interface 170 for processing by the analysis module 150. The analysis module 150 may process the sensor data to determine one or more cardiorespiratory parameters, behavior parameters, and/or health events and provide feedback to the respective sensor module. The analysis module 150 may process the determined cardiorespiratory and/or behavior parameters and/or health events with respect to stored triggering conditions to determine the operation instructions for the respective environmental actuator(s) with regard to the environmental condition changes. The analysis module 150 may transmit those instructions to the respective sensor module 120. In some embodiments, the analysis module 150 may also cause the determined parameters to be displayed on a display (such as a display 140) and/or a display associated with the analysis module 150.

The one or more sensors 122 may be disposed at one or more locations within the defined area. The one or more sensors 122 may be configured to communicate to the communication interface 130. For example, different types of sensors 122 may be disposed at the one or more locations. For example, in a rodent cage, one or more non-contact electric field sensors may be disposed may be disposed at locations of stillness and/or activity. For example, these sensors may be disposed at the nesting area, the feeding area, as well as other areas. The sensor placement can be adapted to characterize time spent in various locations.

In some embodiments, the one or more sensors 122 may monitor the parameters for more than one subject in the defined environment. For example, the processor 124 may differentiate the sensor data using identification information of each subject, such as an RFID tag, location within the defined environment, other physiological parameters (e.g., weight), among others, or a combination thereof.

For example, to uniquely associate a subject (e.g., animal (e.g., mouse)) with its chosen environment (e.g., shelter) and/or sensor data, an identification module (e.g., RFID chips) with identification information that identifies the subject may be disposed on the subject and a reader (e.g., antenna), which can read the identification information and transmit (e.g., at 125-134 KHz) the identification information to a communication interface (e.g., transceiver), may be disposed at a specific location where the subject may be located (e.g., underneath the area (e.g., dish) on which the subject rests). The sensor module 120 may process the sensor data with the associated identification information so that the voltages corresponding to the sensor data is a unique analog voltage for each sensor (e.g. RFID #1=1V; RFID #2=2V; together=3V).

In some embodiments, the module 120 may be configured to monitor two or more defined environments. For example, the defined environments may use the same processor 124, memory 126, environmental actuators 128, communication interface 130, and power source 132 (also referred as processing module). Each defined environment may include one or more sensors 122 and transmit the sensor data received from those sensors 122 to the processor 124.

In some embodiments, the system 100 may include an electrical shielding material and/or metal sheeting material that at least partially surrounds the defined environment. This can improve the measurements from the sensors and allow an area to be partitioned into a plurality of separate sensing environments.

In some embodiments, the electrical shielding material may be disposed on one or more walls/sides within the defined area. The electrical shielding material may include but is not limited to a woven fabric coated with a metal material (e.g., VeilShield fabric), as well as various metals used for electrical shielding and grounding (e.g., Faraday cages). For example, VeilShield (https://www.lessemf.com/fabric3.html) is a woven 132/inch mesh polyester fabric coated with zinc-blackened nickel over copper, and has 0.1 Ohm/sq resistivity. For some embodiments, the defined area may also include metal sheeting disposed on one or more sides of the defined area. The metal sheeting may include a metal mesh shielding, such as a brass metal shielding. For example, the metal shielded may include a brass screening, 16 wires/inch, which can be used in Faraday cages. For example, by including grounded shielding surrounding in individual animal shelters, the sensor data for individual animals in dual housed cages can be recorded with very good signal isolation.

Figure 3:
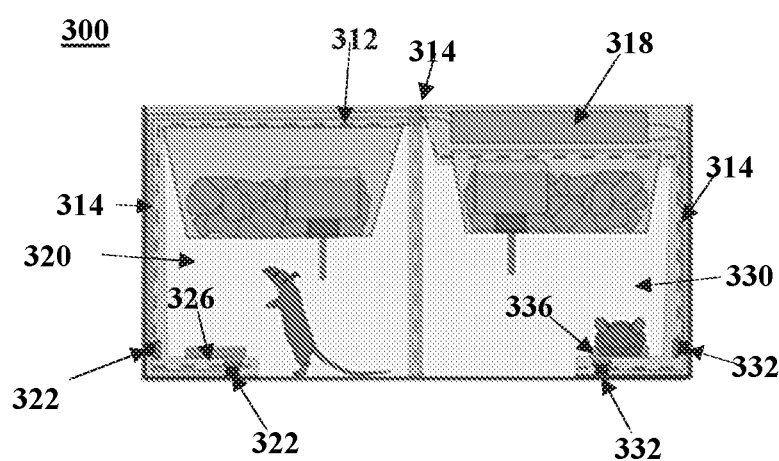
FIG. 3 shows an example of another system configuration according to some embodiments.

In some embodiments, the shielding may be used to partition an area into two or more defined environments. FIG. 3 shows an example a rodent cage 300 in which the shielding partitions a cage into two defined environments. In these cases, recordings from electric field sensors are electrically isolated and embedded in electrically partitioned area with wiring connected to the processor via encased areas inaccessible to animals. The processing module (e.g., processor (e.g., 124), memory (e.g., 126), environmental actuator(s) (e.g., 128), e.g., communication interface (e.g., 130), and power source (e.g., 132)) can be located above the animal environments in an area inaccessible to rodents, for example, just under the cage lid. The one or more sensors and/or actuators may communicate with the processor via wires that are disposed within the encased areas inaccessible to animals, such as the sides. In some embodiments, the one or more sensors and/or actuators may communicate with the processor.

As shown in FIG. 3, the cage 300 can be divided into a first defined environment 320 and a second defined environment 330, for example, by a shielded material 314, such as an electrically shielded translucent polycarbonate sheet, which is illustrated by a broken line. The cage 300 may include the shielded material 314 along most of the walls of the cage 300. The cage 300 may include metal 316 disposed on the sides of the cage 300. The metal 316 and the shielded material 314 may be disposed in areas of the cage that are inaccessible to animals disposed therein.

In this example, the cage 300 may include one or more sensors 322 and 332 near the nest 326 and 336 in the environments 310 and 320, respectively. The one or more sensors 322 and 332 may be non-contact electric field sensors. The one or more sensors 322 may transmit the sensor data to the processing module 318, which includes a processor(s) (e.g., processor(s) 124), memory (e.g., memory 126), environmental actuator(s)(e.g., environmental actuator(s) 128), communication interface (e.g., communication interface 130), and power source (e.g., power source 132). The processing module 318 can also be configured to transmit the received sensor data to an analysis module (e.g., the analysis module 150) for further processing.

By placing the sensors under adjacent animal shelters, the cage 300 can optimize detection of cardiorespiratory parameters in resting animals. Importantly, grounded shielding surrounding these shelters can permit recordings from individual animals in dual housed cages with very good signal isolation.

In some embodiments, the sensor module 120 including the shielding and the metal material may be part of a single unit assembly that is removably attached to and/or disposed within the defined environment. By providing the system 100 as insertable and detachable single unit assemblies that include molding for electrical shielding, home cages can be used and allow for device removal for standard cage washing.

In some embodiments, one or components of the sensor module 120 may be integrated with or fixed to the defined environment or area. For example, the processing module 318 shown in FIG. 3 (e.g., the processor 124, the memory 126, the environmental actuators 128, the communication interface 130, and/or the power source) of a sensor module 120 may be disposed on the top and/or sides of a cage and/or crate. In this example, the power source 132 may be disposed in a pocket under the cage lid, where there is ample room for a battery of the required size.

In some embodiments, for human subjects, the processing module may be provided in a modular container that can be removably disposed within and/or outside the defined environment. The one or more sensors may be fixed with the one or more shielding and metal materials into an object (e.g., a mattress and/or chair cover) to be disposed within an environment.

Figure 4:
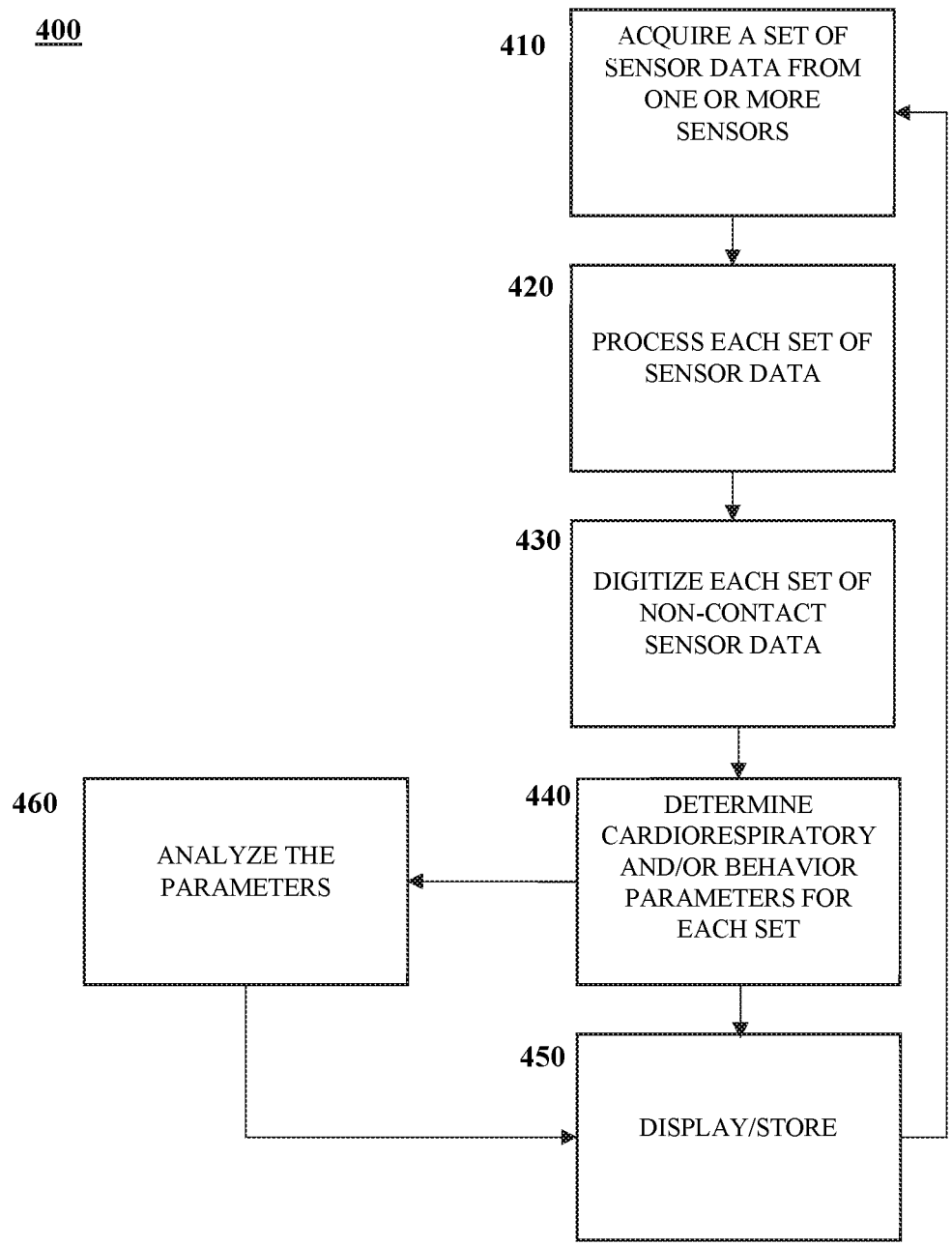
FIG. 4 shows a method of processing the sensor data according to embodiments.
Figure 5:
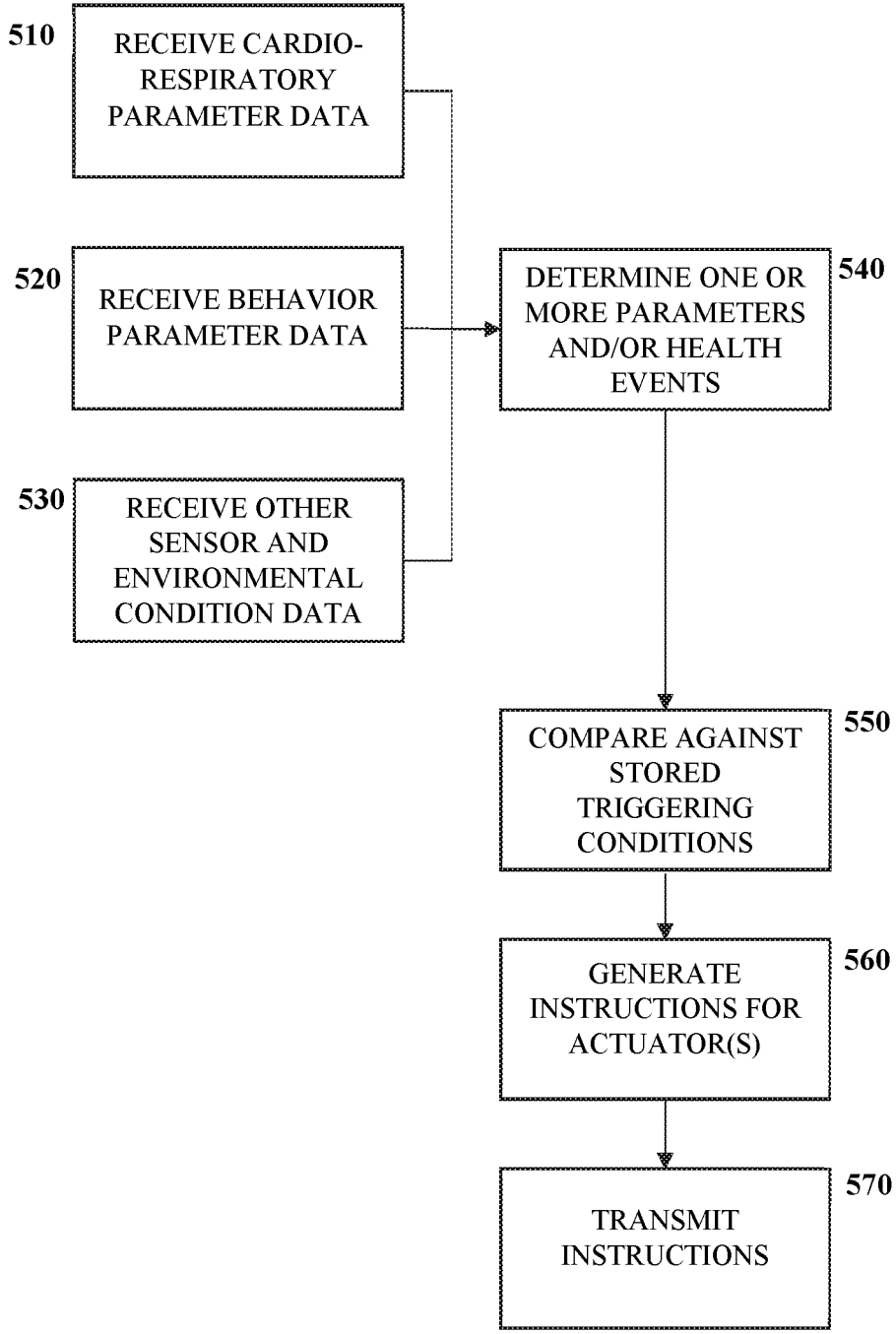
FIG. 5 shows a method of analyzing the sensor data according to embodiments.

FIGS. 4 and 5 show methods of determining one or more cardiorespiratory and/or behavior parameters, and/or health events and generating feedback using sensor data from one or more sensors that includes one or more non-contact electric field sensors. Unless stated otherwise as apparent from the following discussion, it will be appreciated that terms such as "comparing," "modifying," "generating," "determining," "calibrating," "displaying," "obtaining," "processing," "computing," "selecting," "receiving," "detecting," "estimating," "calculating," "quantifying," "outputting," "acquiring," "analyzing," "retrieving," "inputting," "moving," "assessing," "collecting," "storing," "receiving," "performing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. The system for carrying out the embodiments of the methods disclosed herein is not limited to the systems shown in FIGS. 1 and 6. Other systems may also be used.

The methods of the disclosure are not limited to the steps described herein. The steps may be individually modified or omitted, as well as additional steps may be added. It will be also understood that at least some of the steps may be performed in parallel. For example, the methods shown in FIGS. 4 and 5 may be performed for each set or packet of sensor data and therefore the methods for each packet may be performed in parallel.

FIG. 4 shows a method 400 of receiving and processing one or more sets of data received from one or more sensors disposed within a defined environment. As shown in FIG. 4, the method 400 may include a step 410 of acquiring a set or packet of sensor data from one or more sensors. The sensor data may include ("raw" or "analog") sensor data from one or more non-contact electric field sensors, as well as data from other sensors related to the subject (e.g., physiological sensors, feeding sensors, etc.) and/or environmental conditions provided in the defined environment. For example, the module 120 may cause the packet or set of data from a sensor to be transmitted when the amount of data provided in the set or packet meets analysis conditions (e.g., for example, a sample size of packets/sets of data (e.g., sixteen sets of data)) and/or meets certain trigger conditions.

Next, the method 400 may include a step 420 of processing the received sensor data. For example, the "raw" sensor data received from the electric field sensor(s) may be preprocessed using linear filtering to remove out-of-band noise.

After which, the method 400 may include a step of 430 of digitizing each set of analog sensor data. For example, the analog raw electric field sensor data may be converted to digital electric field sensor data.

In some embodiments, the method 400 may include a step 440 of determining cardiorespiratory and/or behavior parameters using the digitized data. In some embodiments, the system 100 can separately analyze the stillness and movement data to determine one or more parameters. For example, the system 100 may segment the digitized non-contact electric field sensor data for a subject into stillness and movement data corresponding to periods of stillness and movement, respectively, based on threshold(s) and/or location of sensor. For example, the digitized data of signals from a non-contact sensor located under the bed would indicate possible period(s) of stillness and initiate a frequency-domain analysis for respiration rate and/or heart rate in step (450). The presence of larger-amplitude signals from non-contact sensors located elsewhere in the cage could indicate periods of movement. For example, for rodents, the data could be in frequency-domain ranges of the signals: 1-6.4 Hz for respiration, 4.3-12 Hz for heartrate, lower frequency for gross movement, 10-25 Hz for chewing.

For stillness data, the system 100 may determine cardiorespiratory parameters by transforming the digitized stillness data into frequency data. For example, the system 100 may apply Fourier transform and Buneman Frequency Estimation to transform the digitized data to frequency data. The system may then determine the heart rate and/or respiratory rate from the frequency content of the signals, and the variability in both rates will be assessed using sliding window (short time) Fourier methods.

For movement data, the system 100 may process the signals in the frequency domain to determine the periodicity, duration of movements, and in the time domain to assess the magnitude and spontaneity of the movements using standard signal detection and extraction processing approaches. For example, the system 100 could use different voltage thresholds and/or range of thresholds to determine movement-related events that are above respiratory and heart rate signal levels. In some embodiments, the system 100 can further process the behavior parameter to determine characteristics of the behavior using threshold-based detection. For example, the characteristics can include calculations of incidence (e.g., of the behavior), amplitude, duration and various mathematically defined features of these behaviors (e.g. rate of rise and decay, duration at half amplitude, instantaneous frequency). Further, the threshold-based detection may include applying logical criteria that separate components (e.g. duration of time above threshold, including via window discriminator to detect and differentiate those above initial threshold but below another threshold, duration of time between events prior to additional triggered detection, etc.). A further elaboration of feature extraction includes software that enables voltage waveform templating and sorting. For example, a given motor behavior may be of the same amplitude and frequency but have a differing duty cycle as seen with various locomotor behaviors that have different duty cycles for the flexion and extension phases of locomotion. In another example, the sensor module and/or analysis module may include a neural network processing system that can be taught stereotypical behaviors such as chewing, grooming, and/or other behaviors using the data to create templates to compare to the digitized sensor data.

In some embodiments, the system 100 may process the digitized data (e.g., stillness and/or movement data), without converting into the frequency data, to determine one or more cardiorespiratory and/or behavior parameters, and/or health events. For example, the system 100 may compare the digitized sensor data to stored templates to determine one or more cardiorespiratory and/or behavior parameters, and/or health events.

The method 400 may optionally include a step 450 of displaying and/or storing the determined parameters, processed sensor data, raw data, or a combination thereof.

After one or more parameters are determined, the method 400 may optionally include a step 460 of further analyzing the sensor data and/or one or more determined cardiorespiratory and/or behavior parameters for additional parameters, one or more health events, and/or one or more feedback instructions. In some embodiments, the one or more processors 122 of the sensor module 120 may perform steps 410-460 and transmit the determined parameters, processed sensor data, raw data, or a combination thereof to the analysis device 150 for further processing in addition to and/or in the alternative to the step of displaying 460. In some embodiments, the one or more processors 122 may perform the analysis step 460. After which, the method 400 may include the step 450 of displaying and/or storing the determined parameters and/or events determined in step 460.

It will be understood that steps 410-460 may be performed for each set of sensor data collected by one or more sensors.

FIG. 5 shows a method 500 of analyzing one or more sets of processed data received from one or more sensors disposed within a defined environment to determine one or more cardiorespiratory, one or more behavior parameters, one or more health events, one or more triggering conditions, one or more operation instructions for the actuators regarding the environmental conditions of the defined environment, among others, or a combination thereof. As shown in FIG. 5, the method 500 may receive the cardiorespiratory parameter data (e.g., unprocessed and/or processed stillness data and/or cardiorespiratory parameters determined in step 440) 510; the behavior parameter data (e.g., unprocessed behavior movement data and behavior parameters determined in step 440) 520; and/or raw sensor data and/or other sensor and/or environmental condition data (e.g., received from the one or more sensors 122 in step 410) 530; among others, or a combination thereof. The sensor data may include ("raw" or "analog") sensor data from one or more non-contact electric field sensors, as well as data from other sensors related to the subject (e.g., physiological sensors, feeding sensors, etc.) and/or environmental conditions (e.g., temperature, humidity level, light level, noise/sound level, etc.) provided in the defined environment.

Next, the method 500 may include a step 540 of determining one or more cardiorespiratory parameters (e.g. heart rate, respiratory rate, heart rate variability), behavior parameters, health events, and/or environmental events, and/or characteristics thereof (e.g., duration, severity, and variability in detectable events such as those listed below etc.) using the data 510, 520, and/or 530. For example, the system 500 may determine cage humidity, cage temperature, respiratory rate, heart rate, heart rate variability, sleep state, blood pressure, eating state (e.g., receive time eating), behavioral state, specific motor behavior (e.g. whisking, drinking, eating, excretion, exploratory behavior, grooming, mounting, shivering, locomotion, etc.), neurological state (e.g., tremors, dyskinesias, wet dog shakes, etc.), among others, or a combination thereof.

For example, to determine blood pressure of a subject, the system 100 may further include recordings of variations in blood pressure using two or more sensors disposed within the environment (e.g., shelter) along the arterial branch (e.g. underneath an animal at rest with one sensor positioned underneath the aortic arch and the other at the abdominal aorta). These sensors provide recordings of arterial pulse pressure waves. The system may then pulse wave velocity (PVW) from these recordings.

The method 500 may include a step 550 of comparing the determined cardiorespiratory and/or health parameter(s) and/or health event(s) to the one or more stored triggering conditions (e.g., light, auditory, feeding, etc.) to determine operation instruction(s) for any changes to the environmental conditions within the defined environment. The triggering conditions may be default and/or selected by the user (e.g., the researcher). The triggering conditions may be associated with operation instruction(s) for one or more changes in the environment when the determined parameter and/or health event is above, below, and/or meets specific criteria.

Based on that comparison, the method 500 may include a step 560 of generating operation instructions for the one or more actuators 128. For example, the system 100 may instruct an LED light to illuminate and/or turn off, deliver a drug/odorant, change the dosage of a drug, among others, or a combination thereof, based on determined parameters and/or health state and the stored triggering conditions.

For example, if the methods 400 and 500 are performed in a closed loop, the system 100 can perform respiratory-rate based modulation of cage temperature. For example, the system may apply a proportional-integral-derivative (PID) control loop, with the estimated respiratory rate (RR) as the input variable, and the temperature of the cage as the output variable. Safety limits can be used to ensure that the temperature does not reach unsafe values (either too high or too low) for the animals. Before implementing the closed-loop control, the relationship between cage temperature and RR can be established for each individual subject as part of a calibration procedure. One animal subject (e.g., rodent) per littermate pair can be assigned RR-based temperature control. Individual subjects can be identified by subcutaneous RFID tag. RFID tag detection can pair the appropriate animal subject to the shelter used for temperature control. For example, using this control loop, if the respiratory rate is less than or equal to, for example, 60 breaths/minute for 2 seconds, the system 100 may cause the temperature within the defined environment to increase, for example, 2° C. for 5 minutes.

In some embodiments, one of more of the triggering conditions may relate to facilitating relaxation, for example, by being associated with operating instructions for controlling the light panel. The continuous recordings of respiratory rate when an animal is at rest can be used in a feedback-based control of a triggering condition of an operation instruction (e.g. turning off a light) to reinforce lower frequency breathing rates that facilitate relaxation. For example, for rodent cages, the system 100 may cause an ongoing flickering LED light panel on the cage to turn off when the respiratory rate is below a threshold (e.g., RR less than or equal to 80 breaths/min).

In some embodiments, one or more of the triggering conditions may relate to preventing hypertension by being associated with operating instructions for controlling the light panel to control the respiration rate, the activity level, and/or food preference-based control of a subject. For example, just as animals presented with bright light as a negative stimulus can be trained to undergo slowed RR (described above), animals/individuals could similarly be trained to positive or negative stimuli in order to increase/decrease motor activity, or increase/decrease caloric intake etc. In the example described above, those trained to increase motor activity and/or decreased caloric intake may lead to a corresponding reduction in body weight (e.g. reduced obesity) and blood pressure (e.g. control of hypertension).

For example, just as the system may control the respiration as discussed above to facilitate relaxation, the system 100 may be configured to cause an increase in the activity level by shutting off the flickering LED panel based on exceeding a threshold of total motor activity/preset epoch (e.g., five minutes) (i.e., a triggering condition). For example, the movement data (i.e., digitized sensor data) can be stored and examined at periodic intervals, e.g. every 30 seconds, and integrated over the period to produce a value representing average activity/movement. Then, for example, using voltage thresholding, the system 100 may cause the LED light panel on the cage to turn off when the activity level meets the following triggering condition: it is above a preset epoch (e.g., values that are above threshold detection of movement for 20% (equivalent to activity for one of the five minutes in the defined preset epoch above)).

Similarly, the system 100 may cause a food-preference based control based on the received ratio for time eating high fat/normal diet (e.g., per hour). For example, the home cage can contain two distinct food delivery sites with distinct sensors at each site. One channel of data from each sensor can be digitized and analyzed in the time domain for amplitude, indicating presence of the animal by its movement, and in the frequency domain for frequencies characteristic of reaching for the food pellet (0.1-3 Hz) and for chewing (10-25 Hz). A positive result of this analysis may be binned at, e.g. 1 second intervals, and accumulated. Total time at each station can thus be calculated. The system can process the data by comparing the data with a triggering condition (e.g., threshold(s)) to identify when an animal's eating at the high fat or normal diet site. Threshold-based detection of eating at the high fat diet may be used to activate flickering LED light panel as a negative stimulus. Conversely or in addition, threshold based detection of eating at the normal diet site could be used to trigger a dimming or turning off of the LED light.

In some embodiments, one or more of the triggering conditions may relate to predicting and preventing epileptic disorders. For example, the system may monitor heart rate and respiratory rate, and trigger an alarm (i.e., an operation instruction) when the received heart rate during inhalation to the heart rate during exhalation is not cyclical for a number of epochs.

In some embodiments, one or more of the triggering conditions may relate to diagnosing, predicting and/or preventing sleep disorders by releasing an odorant (i.e., associated operation instruction) that reduces stress (e.g., oxytocin) and/or changing medication dose. For example, the system 100 may monitor the respiratory rate and heart rate, and cause the odorant to be delivered when the received heart rate during inhalation to the heart rate during exhalation meets the triggering condition—it is not cyclical for a number of epochs.

By way of another example, the system 100 may monitor durations of sleep—including discrimination of REM and non-REM sleep—by monitoring respiratory rate. The triggering conditions may include a specific duration of non-REM or REM sleep per bout, per hour or per day. The system may cause the change of dosage of a drug when total sleep bout—or duration of non-REM or REM sleep per bout—is less than a stored duration prior to drug dosing (e.g. per sleep bout, per hour or per day). This occurrence can be determined to be a change toward desired sleep structure.

Additionally, the system can use RFID tag detection to allow pairing of the appropriate animal to the defined environment for RR conditioning via a voltage trigger pulse that maintains the conditioning paradigm until RFID detection is lost. Therefore, duration and number of conditioning periods can be directly linked to time spent in the cage.

If steps 540-560 are being performed by a remote analysis module (e.g., module 150), the method 500 may include a step 570 of transmitting the operation instruction(s) associated with the triggering condition(s) for the actuator(s) 128 generated in step 560 to the sensor module 120. The sensor module 120 may then cause the change in and/or delivery of the environmental conditions in the defined space based on the transmitted operation instructions.

Figure 6:
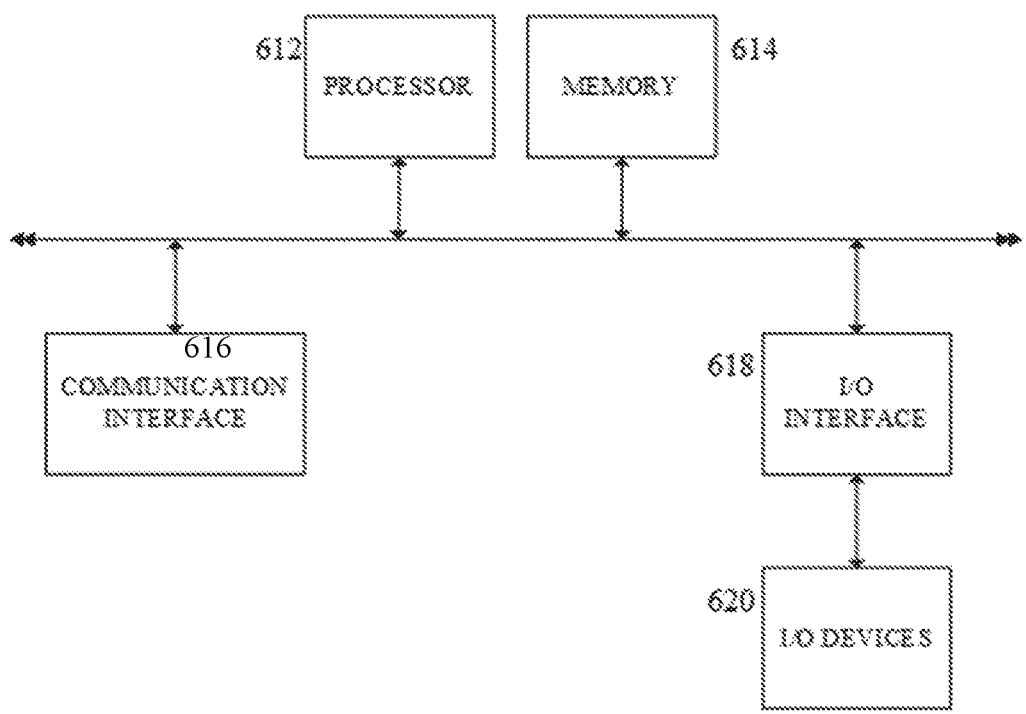
FIG. 6 shows a block diagram illustrating an example of a computing system.

One or more of the devices and/or systems of the system 100 may be and/or include a computer system and/or device. FIG. 6 is a block diagram showing an example of a computer system 600. The modules of the computer system 600 may be included in at least some of the systems and/or modules, as well as other devices and/or systems of the system 100.

The system for carrying out the embodiments of the methods disclosed herein is not limited to the systems shown in FIGS. 1 and 6. Other systems may also be used. It is also to be understood that the system 600 may omit any of the modules illustrated and/or may include additional modules not shown.

The system 600 shown in FIG. 6 may include any number of modules that communicate with each other through electrical or data connections (not shown). In some embodiments, the modules may be connected via any network (e.g., wired network, wireless network, or a combination thereof).

The system 600 may be a computing system, such as a workstation, computer, or the like. The system 600 may include one or more processors 612. The processor(s) 612 (also referred to as central processing units, or CPUs) may be any known central processing unit, a processor, or a microprocessor. The CPU 612 may be coupled directly or indirectly to one or more computer-readable storage media (e.g., memory) 614. The memory 614 may include random access memory (RAM), read only memory (ROM), disk drive, tape drive, etc., or a combinations thereof. The memory 614 may be configured to store programs and data, including data structures. In some embodiments, the memory 614 may also include a frame buffer for storing data arrays.

In some embodiments, another computer system may assume the data analysis or other functions of the CPU 612. In response to commands received from an input device, the programs or data stored in the memory 614 may be archived in long term storage or may be further processed by the processor and presented on a display.

In some embodiments, the system 600 may include a communication interface 616 configured to conduct receiving and transmitting of data between other modules on the system and/or network. The communication interface 616 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 610 may include an input/output interface 618 configured for receiving information from one or more input devices 620 (e.g., a keyboard, a mouse, and the like) and/or conveying information to one or more output devices 620 (e.g., a printer, a CD writer, a DVD writer, portable flash memory, etc.). In some embodiments, the one or more input devices 620 may be configured to control, for example, the generation of the management plan and/or prompt, the display of the management plan and/or prompt on a display, the printing of the management plan and/or prompt by a printer interface, the transmission of a management plan and/or prompt, among other things.

In some embodiments, the disclosed methods (e.g., FIGS. 4 and 5) may be implemented using software applications that are stored in a memory and executed by a processor (e.g., CPU) provided on the system 100. In some embodiments, the disclosed methods may be implemented using software applications that are stored in memories and executed by CPUs distributed across the system.

As such, any of the systems and/or modules of the system 100 may be a general purpose computer system, such as system 600, that becomes a specific purpose computer system when executing the routines and methods of the disclosure. The systems and/or modules of the system 100 may also include an operating system and micro instruction code. The various processes and functions described herein may either be part of the micro instruction code or part of the application program or routine (or combination thereof) that is executed via the operating system.

If written in a programming language conforming to a recognized standard, sequences of instructions designed to implement the methods may be compiled for execution on a variety of hardware systems and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 1 and 6. It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A system for monitoring one or more cardiorespiratory parameters, behavior parameters, and health events based on the cardiorespiratory and/or behavior parameters, associated with each subject in one or more defined environments, the system comprising:

one or more sensor modules disposed within and/or on the one or more defined environments, each sensor module including:
one or more sensors disposed at a specific spatial location in the one or more defined environments and configured to record sensor data of each subject, the one or more sensors including one or more non-contact electric field sensors, the one or more non-contact electric field sensors configured to record non-contact sensor data related to one or more periods of stillness and/or movement as analog electric field sensor data; and one or more processors configured to convert the analog electric field sensor data to digital electric field sensor data to determine at least cardiorespiratory parameters and/or behavior parameters using the non-contact sensor data;

a cage, the cage including the one or more defined environments, the cage including a first defined environment and a second defined environment separated by the first defined environment by an electrical shielding material;

each of the first defined environment and the second defined environment includes the one or more sensors; and a processor module disposed on the cage, the processor module including the one or more processors, the processor module being configured to communicate with each of the one or more sensors disposed in the first defined environment and the second defined environment;

wherein the one or more processors is configured to determine one or more cardiorespiratory parameters when the non-contact sensor data relates to one or more periods of stillness, the one or more cardiorespiratory parameters includes respiratory rate and heart rate.

2. The system according to claim 1, wherein:

the one or more processors is configured to determine whether the non-contact sensor data relates to the one or more periods of stillness and/or movement based one or more thresholds and/or a location of the one or more non-contact sensors within each defined environment; and when the one or more processors determines that the non-contact sensor relates to the one or more periods of movement, the one or more processors is configured to determine the one or more behavior parameters.

3. The system according claim 1, further comprising:

one or more environmental actuators configured to cause a change in one or more environmental conditions within each defined environment and/or deliver an alert according to operation instructions based on (i) stored triggering conditions and (ii) the non-contact sensor data, the one or more cardiorespiratory parameters, and/or the one or more behavior parameters.

4. The system according to claim 3, wherein the one or more processors is configured to determine the operation instructions by comparing at least the non-contact sensor data to the stored triggering conditions.

5. The system according to claim 1, wherein:

the one or more defined environments includes:
 a metal shielding material; and
 the electrical shielding material;

the metal shielding material and/or the electrical shielding material at least partially surround each defined environment.

6. The system according to claim 1, further comprising:

a display, the display configured to display the non-contact sensor data and/or the one or more cardiorespiratory parameters for the first defined environment and the second defined environment.

7. The system according to claim 1, wherein the one or more sensor modules includes a communication interface and one or more environmental actuators configured to cause a change in one or more environmental conditions within each defined environment based on one or more operating instructions, and wherein the system further comprises:

an analysis module including a processor that is configured to receive the sensor data from the one or more sensor modules using the communication interface;

wherein the analysis module is configured to compare (i) at least the non-contact sensor data, the one or more cardiorespiratory parameters, and/or the one or more behavior parameters to (ii) one or more stored triggering conditions to determine the one or more operating conditions.

8. The system according to claim 1, wherein the one or more sensors includes tracking sensors configured to detect each subject with respect to each defined environment, a location of each subject within each defined environment, among others, or a combination thereof.

9. A method for monitoring one or more cardiorespiratory parameters, behavior parameters, and health events based on the cardiorespiratory and/or behavior parameters, associated with teach subject disposed in one or more defined environments, the method comprising:

acquiring sensor data from one or more sensor modules disposed within and/or on the one or more defined environments, each sensor module including one or more sensors disposed at a specific spatial location in the one or more defined environments and configured to record sensor data of each subject, the one or more sensors including one or more non-contact electric field sensors, the one or more non-contact electric field sensors configured to record non-contact sensor data related to one or more periods of stillness and/or movement as analog electric field sensor data; and converting, using one or more processors, the analog electric field sensor data to digital electric field sensor data to determine at least cardiorespiratory parameters and/or behavior parameters using the non-contact sensor data;

wherein the one or more cardiorespiratory parameters is determined when the non-contact sensor data relates to one or more periods of stillness, the one or more cardiorespiratory parameters includes respiratory rate and heartrate;

wherein the one or more defined environments is disposed in a cage, the cage includes a first defined environment and a second defined environment separated by the first defined environment by an electrical shielding material;

wherein each of the first defined environment and the second defined environment includes the one or more sensors;

wherein a processor module is disposed on the cage, the processor module including the one or more processors, the processor module being configured to communicate with each of the one or more sensors disposed in the first defined environment and the second defined environment; and wherein the acquiring the sensor data includes receiving, at the processor module, the sensor data from each of the one or more sensors disposed in the first defined environment and the second defined environment.

10. The method according to claim 9, wherein:

the non-contact sensor data is determined to relate the one or more periods of stillness and/or movement based one or more thresholds and/or a location of the one or more non-contact sensors within each defined environment; and when the one or more processors determines that the non-contact sensor relates to the one or more periods of movement, the one or more processors is configured to determine the one or more behavior parameters.

11. The method according to claim 9, further comprising: instructing one or more environmental actuators to cause a change in one or more environmental conditions within each defined environment and/or deliver an alert according to operation instructions based on (i) stored triggering conditions and (ii) the non-contact sensor data, the one or more cardiorespiratory parameters, and/or the one or more behavior parameters.

12. The method according to claim 11, further comprising:
determining the operation instructions by comparing at least the non-contact sensor data to the stored triggering conditions.

13. The method according to claim 9, wherein:
the one or more defined environments includes:
a metal shielding material; and
the electrical shielding material; and
the metal shielding material and/or the electrical shielding material at least partially surround each defined environment.

14. The method according to claim 9, further comprising:
displaying the non-contact sensor data and/or the one or more cardiorespiratory parameters for the first defined environment and the second defined environment.

15. The method according to claim 9, further comprising:
comparing the (i) at least the non-contact sensor data, the one or more cardiorespiratory parameters, and/or the one or more behavior parameters to (ii) one or more stored triggering conditions to determine one or more operating conditions; and
causing a change in one or more environmental conditions within each defined environment based on the one or more operating instructions.

16. The method according to claim 9, wherein the one or more sensors includes tracking sensors configured to detect each subject using identification information, with respect to each defined environment, a location of each subject within each defined environment, among others, or a combination thereof; and the method further comprises:
associating the identification information to the sensor data for the subject.

17. The system according to claim 1, wherein each non-contact electric field sensor is an electric potential integrated circuit sensor.

18. The method according to claim 9, wherein each non-contact electric field sensor is an electric potential integrated circuit sensor.

* * * * *

UNITED STATES PATENT AND TRADEMARK OFFICE
CERTIFICATE OF CORRECTION

| | | |
|---|---|---|
| PATENT NO. | : 11,510,593 B2 | Page 1 of 1 |
| APPLICATION NO. | : 16/095906 | |
| DATED | : November 29, 2022 | |
| INVENTOR(S) | : Hochman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 774 days.

Signed and Sealed this
Fourteenth Day of January, 2025

Derrick Brent
*Acting Director of the United States Patent and Trademark Office*